(12) United States Patent
Fee

(10) Patent No.: US 6,366,803 B1
(45) Date of Patent: Apr. 2, 2002

(54) PREDICTIVE PROBE STABILIZATION RELATIVE TO SUBJECT MOVEMENT

(75) Inventor: Michale Sean Fee, New Vernon, NJ (US)

(73) Assignee: Agere Systems Guardian Corp., Orlando, FL (US)

( * ) Notice: Subject to any disclaimer, the term of this patent is extended or adjusted under 35 U.S.C. 154(b) by 0 days.

(21) Appl. No.: 09/470,861

(22) Filed: Dec. 23, 1999

(51) Int. Cl.⁷ .................................................. A61B 5/04
(52) U.S. Cl. ........................ 600/509; 600/534; 600/547; 600/544; 128/898; 128/920; 901/9
(58) Field of Search ................................. 600/424, 483, 600/544, 300, 301, 481, 484, 509, 529, 534, 547, 552, 587, 114, 117, 118; 128/899, 897, 898, 920; 356/614; 901/9

(56) References Cited

U.S. PATENT DOCUMENTS

| | | | | |
|---|---|---|---|---|
| 5,797,849 A | * | 8/1998 | Vesely et al. ................ | 600/461 |
| 5,840,025 A | * | 11/1998 | Ben-Haim .................. | 600/424 |
| 6,016,439 A | * | 1/2000 | Acker ........................ | 600/411 |
| 6,266,551 B1 | * | 7/2001 | Osadchy et al. ............ | 600/424 |

* cited by examiner

Primary Examiner—Kennedy Schaetzle
(74) Attorney, Agent, or Firm—Nancy R. Gamburd

(57) ABSTRACT

The present invention provides a method and system to actively or predictively stabilize a probe, such as a microelectrode, relative to movement of the subject. In the preferred embodiments, cardiac and respiratory activities of the subject are measured and utilized to predict subject movement. In the preferred embodiments, a probe is mounted on a manipulator such that the probe moveable in response to a control voltage. A calibrated control voltage is determined from a known probe displacement, such as by measuring probe impedance during a probe oscillation having a known amplitude and frequency. A plurality of control voltage parameters, such as filter coefficients, are then determined from the calibrated control voltage and from a respective measured biological function, such as from an EKG or a thoracic pressure measurement. The control voltage for the probe is then generated from the respective measured biological function and from the respective plurality of control voltage parameters. When more than one measured biological function is utilized, the overall control voltage is a linear superposition of respective intermediate control voltages. The probe is then moved in response to the control voltage, providing stabilization relative to subject movement, and the probe may then be utilized for desired measurements within the subject.

36 Claims, 3 Drawing Sheets

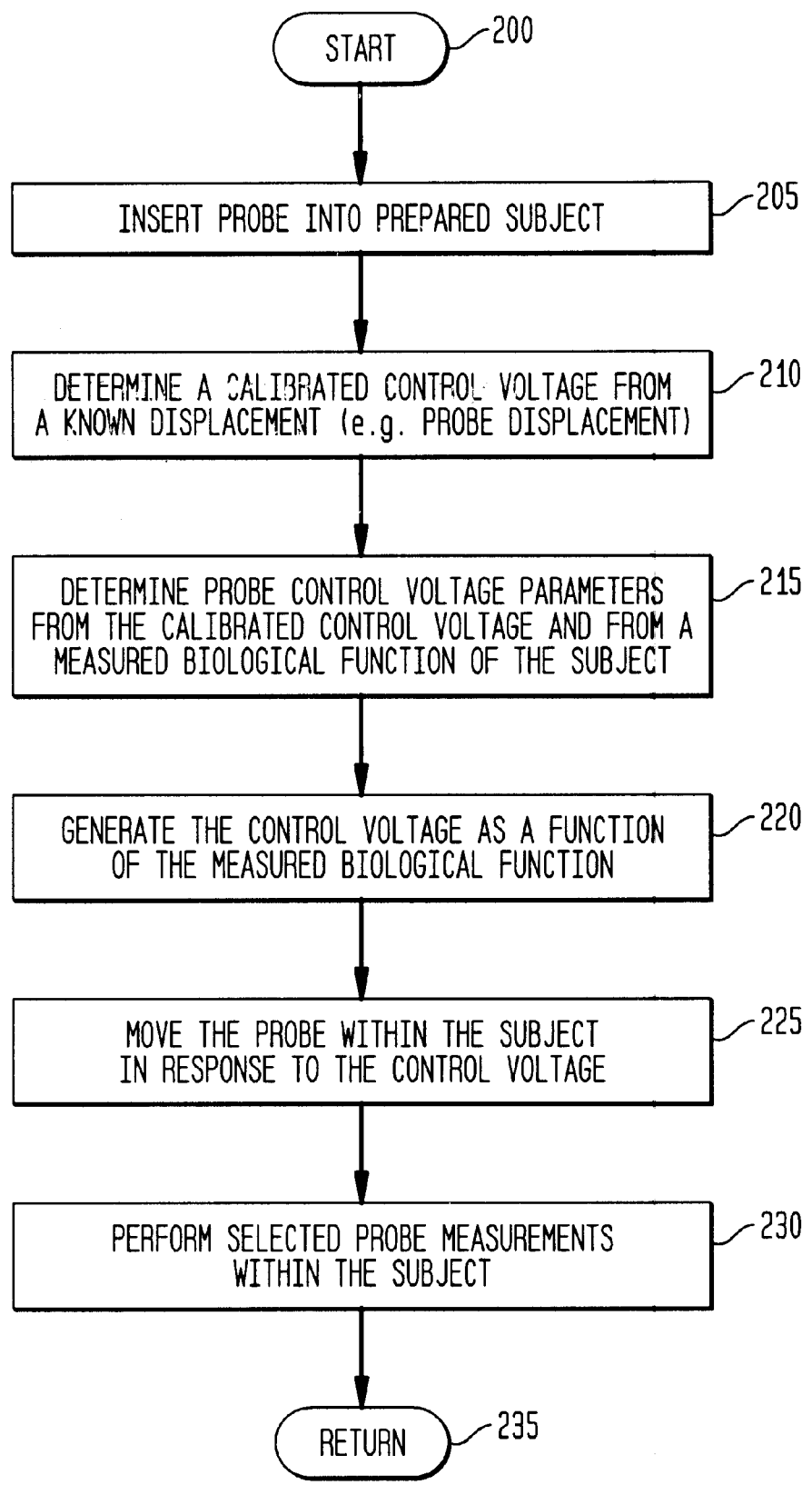

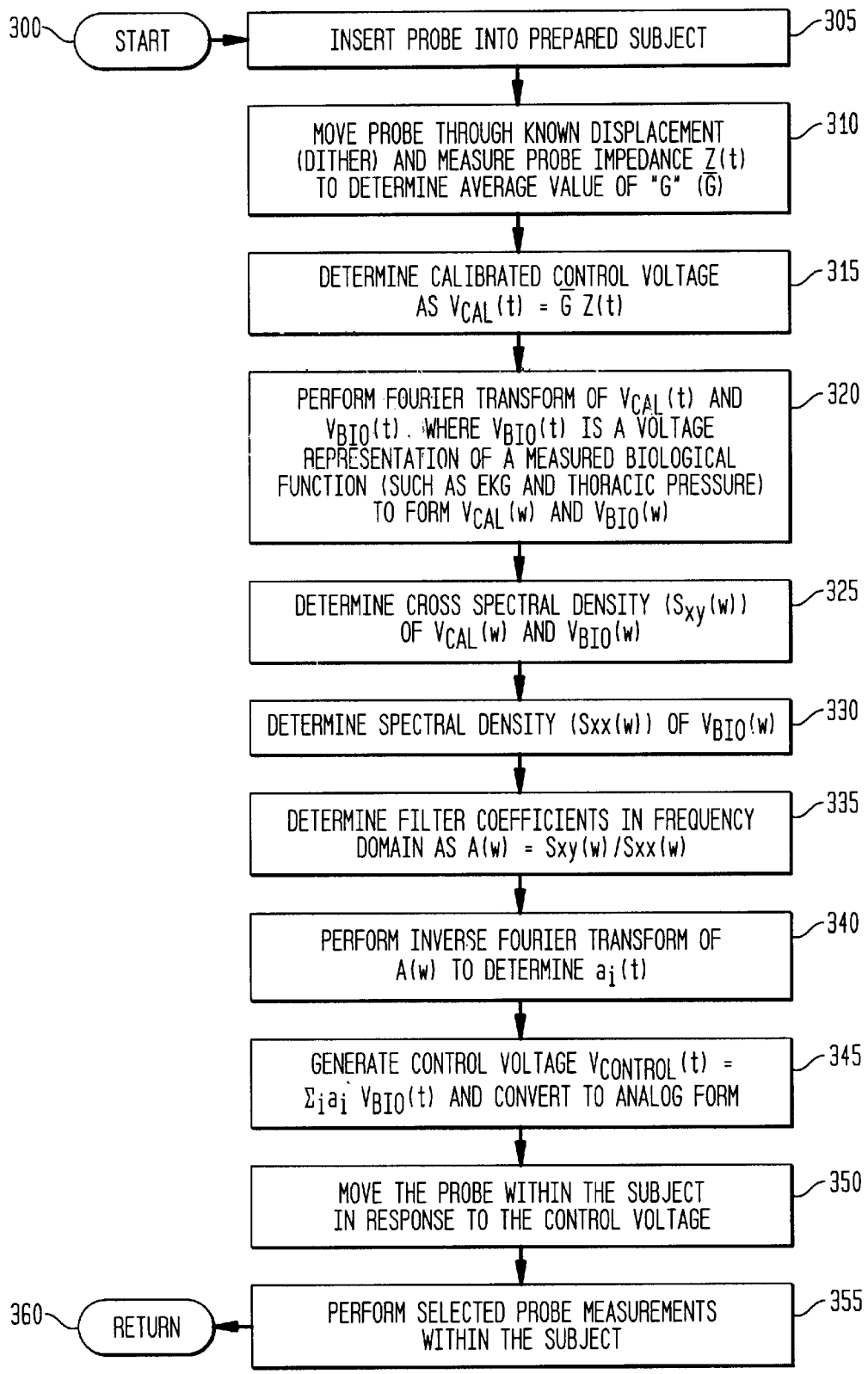

PREDICTIVE PROBE STABILIZATION RELATIVE TO SUBJECT MOVEMENT

CROSS-REFERENCE TO RELATED APPLICATION

The present invention is related to Fee, U.S. patent application Ser. No. 09/472,326, entitled "Interferometric Probe Stabilization Relative to Subject Movement", filed concurrently herewith and commonly assigned to Lucent Technologies, Inc., and incorporated by reference herein, with priority claimed for all commonly disclosed subject matter (the "related application").

FIELD OF THE INVENTION

The present invention relates, in general, to probe stabilization relative to movement of a subject. More particularly, the present invention relates to predictive stabilization, of an intracellular probe, relative to the movement of the subject.

BACKGROUND OF THE INVENTION

Much of our understanding of the function of the brain has come from probing the nervous system at the level of single neurons. With few exceptions, the study of single neurons in behaving animals has been limited to extracellular recordings of action potentials. Action potentials, however, represent only the final, output state of a neuron whose response is essentially determined by the electrical and chemical interactions between smaller, functionally distinct neuronal compartments such as synapses, dendrites, and somata. Nearly all experimental information about the properties and behavior of neurons at this level comes from in-vitro and cell culture experiments. Furthermore, it is known that neuronal integration and firing properties are modulated by neuromodulatory influences and other activities. As a consequence, complete understanding of brain function ultimately requires observation of neuronal compartments and their interactions in intact, live and behaving subject animals.

Problems with mechanical stability make observations of neurons much more difficult in whole-animal preparations than in in-vitro or cell culture preparations. Many structures of interest in neurons are small (on the order of 1 to 10 microns in size), and because electrical and optical probes must be positioned near or inside the cell membrane to function, high quality and long lasting recordings require stable mechanical placement of the probe relative to the tissue. Drift or motion of the electrode or other probe relative to the recorded cell may interfere with good probe penetrations or seals on a neuron. Even when good penetration or seal is achieved, motion may also cause large variations in the recorded signals, degrade the health of the cell, and limit the duration of the recording.

Although a number studies have been published that involve intracellular recordings in anesthetized animals and even awake animals, brain motion makes intracellular recording difficult under even the best conditions. In all these experiments, the essential means of stabilizing the brain is to restrain the head of the animal with a stainless steel plate or pin secured to the cranium. Brain motion in such a head-fixed preparation arises from forces of two origins; first, spontaneous motor behavior of the animal, and second, from periodic physiological processes such as cardiac or respiratory pulsations. These forces may be coupled to the brain in several ways. The cranium and its attachment to the apparatus are both compliant and will move in response to spontaneous and respiratory movements. Forces may also be coupled to the brain through the spinal cord and cerebral spinal fluid. In addition, cardiac pulsations are probably mediated by changes in the volume of cerebral blood vessels. A number of techniques have been developed to permit stable neuronal recordings in the presence of these sources of movement, including draining of the cerebrospinal fluid, mechanical stabilization of the brain or spinal cord, or passive tracking of the probe electrode. Some of these methods, however, accommodate only gross animal movement by restraining the subject, potentially interfering with desired measurements. Other methods may damage fragile brain tissue, or interfere with the subject under study and potentially affect the resulting measurements. In addition, such methods for surface stabilization typically do not account for internal subject movement at a deeper tissue level.

As a consequence, a need remains to provide a method and system for probe stabilization, relative to subject movement, to provide for accurate measurement within a live subject. The method and system should be predictive or active, anticipating subject movement which may otherwise interfere with accurate measurements. In addition, the method and system should not alter or interfere with the physiological states of the subject, and should otherwise minimize contact with the subject tissue, to avoid interfering with the processes under study, to avoid tissue damage, and also to avoid other potential sources of error.

SUMMARY OF THE INVENTION

In accordance with the present invention, a method and system are provided for predictive or active probe stabilization, for anticipating subject movement which may otherwise interfere with accurate measurements. In addition, the method and system of the present invention do not alter or interfere with the physiological states of the subject, and otherwise minimizes contact with the subject tissue, to avoid interfering with the processes under study, to avoid tissue damage, and also to avoid other potential sources of error.

In the preferred method and system for predictive probe stabilization, a probe (such as a microelectrode) is mounted on a piezoelectric manipulator and inserted into the subject, so that the probe is moveable in response to a control voltage. A calibrated control voltage is then determined from a known probe displacement, generally by measuring probe impedance as the probe is oscillated (dithered) with a known amplitude and frequency.

A plurality of control voltage parameters, such as finite impulse response filter coefficients, are determined from the calibrated control voltage and from a measured biological function of the subject. In the preferred embodiment, two measured biological functions are utilized: first, cardiac function, as measured by an electrocardiogram; and second, respiratory function, as measured by thoracic pressure. For each of these measured biological functions, a corresponding plurality of control voltage parameters are determined.

The control voltage to the manipulator holding the probe is then generated from the measured biological function and from the plurality of control voltage parameters. When more than one measured biological function is utilized, such as both an EKG and thoracic pressure, then corresponding intermediate control voltages are generated for each measured biological function. The resulting or overall control voltage is then generated as a linear superposition of the intermediate control voltages. The probe is then moved in response to the control voltage, providing stabilization relative to subject movement, and the probe may then be utilized for desired measurements within the subject.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 2 is a flow diagram illustrating a method for predictive probe stabilization relative to subject movement in accordance with the present invention.

FIG. 3 is a flow diagram illustrating, in greater detail, a preferred method for predictive probe stabilization relative to subject movement in accordance with the present invention.

DETAILED DESCRIPTION OF THE INVENTION

Figure 1:
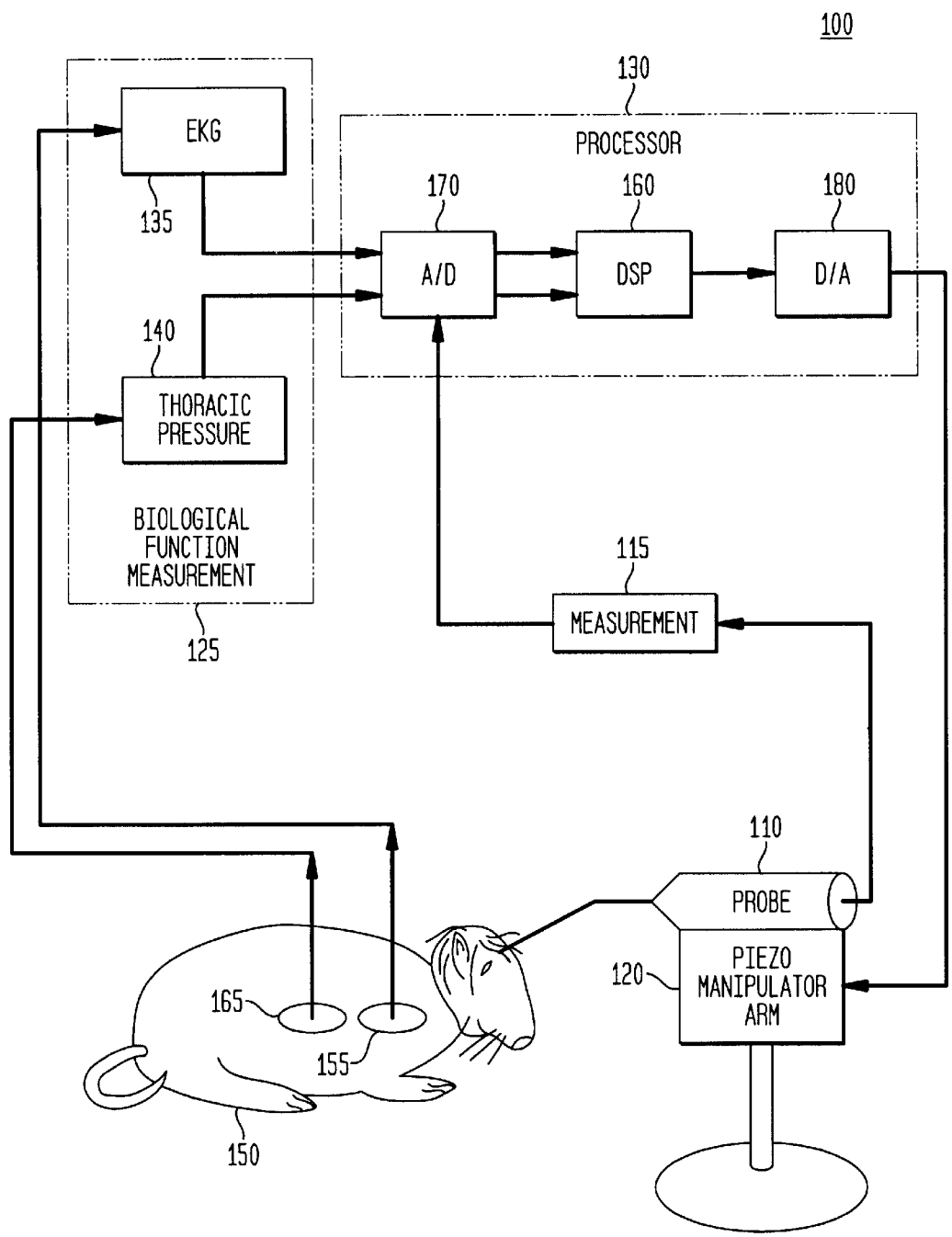
FIG. 1 is a block diagram illustrating a system for predictive probe stabilization relative to subject movement in accordance with the present invention.

While the present invention is susceptible of embodiment in many different forms, there are shown in the drawings and will be described herein in detail specific embodiments thereof, with the understanding that the present disclosure is to be considered as an exemplification of the principles of the invention and is not intended to limit the invention to the specific embodiments illustrated.

As mentioned above, a need remains to provide a method and system for probe stabilization, relative to subject movement, to provide for accurate measurement within a live subject. In accordance with the present invention, a method and system are provided for predictive or active probe stabilization, anticipating subject movement which may otherwise interfere with accurate measurements. In addition, the method and system of the present invention do not alter or interfere with the physiological states of the subject, and otherwise minimizes contact with the subject tissue, to avoid interfering with the processes under study, to avoid tissue damage, and also to avoid other potential sources of error.

An underlying observation of the present invention is that for intracellular probe recording in awake animal subjects, cardiac and respiratory pulsations are often sufficiently large to prevent stable recordings, even in anesthetized subjects. These sources of brain motion, particularly cardiac pulsations, are not strongly coupled to the brain through cranial movement, so probe stabilization techniques involving gross cranial movement detection, such as in the related application, are inapplicable. First, in accordance with the present invention, these periodic physiological sources of motion are readily monitored by standard techniques, such as the electrocardiogram (EKG) and thoracic pressure. Secondly, the relationship between these signals and brain pulsation is fairly stable, making them highly predictive of brain motion. In accordance with the present invention, signals from these measured biological function are used to continuously adjust the electrode position once the relationship between the signal and brain motion is known. As discussed in greater detail below, the general procedure of the present invention is to filter the cardiac and respiratory signals with an arbitrary linear filter to generate a control voltage for a piezoelectric manipulator attached to the probe, thus producing the desired compensatory electrode motion.

The filter parameters are determined in a preliminary step during which the electrode impedance is used as a measure of brain motion. Once the filter parameters are determined from direct measurement of brain motion, the probe (electrode) moved by the piezoelectric arm in response to the measured biological functions (EKG and thoracic pressure), and the probe is then used for the desired or selected intracellular measurement in the subject. recording.

FIG. 1 is a block diagram illustrating a system 100 for predictive probe stabilization relative to subject 150 movement in accordance with the present invention. The system 100 includes a processor 130, biological function measurement 125, and a probe 110 mounted or otherwise attached to a moveable piezoelectric manipulator (arm) 120. The probe 110 is typically inserted into the subject 150 for calibration measurements and for subsequent desired measurements (115), in accordance with the present invention. Alternatively, another device may be utilized for calibration measurements, with the probe 110 utilized for the subsequent, desired measurements. As used herein, the probe 110 may be any one or more of a wide variety of devices requiring stabilization to achieve its intended purpose. For example, the probe 110. may be an intracellular electrode (or microelectrode), with stabilization in accordance with the present invention for accurate intracellular recordings. In other embodiments, the probe 110 may be a surgical instrument, a microscopic instrument, a microscope (such as a two photon scanning laser microscope), a fiber optic scope, or any other device for which relative stabilization is necessary or desirable.

As mentioned above, the biological function measurement(s) 125 of the preferred embodiment includes an electrocardiogram (EKG) 135 and thoracic pressure 140, respectively utilizing corresponding 'standard electrodes 155 and pressure monitor or detector 165, which may be removeably attached to the subject 150. Signals from the EKG 135 and thoracic pressure 140 are input into the processor 130, along with measurements 115 from the probe 110, to calibrate a control voltage, which is utilized subsequently to control the piezoelectric manipulator 120 of the system 100, as discussed in greater detail below. It should be noted that the device utilized for such calibration measurements, which in the preferred embodiment is the probe 110, may be either the same or a different device than the device which is to be stabilized (which in the preferred embodiment is also the probe 110). Also in the preferred embodiment, the piezoelectric manipulator 120 should have (generally) a linear response to the input control voltage. Following such calibration, the control voltage is generated based upon these biological function measurements, without further input from the probe 115 itself (as the probe 115 is then utilized for the selected or desired measurements within the subject 150). The piezoelectric manipulator 120, coupled to the probe 110, moves in response to the control voltage, thereby predictively moving the probe 110 relative to subject movement (as measured by the EKG 135 and thoracic pressure 140).

Continuing to refer to FIG. 1, the processor 130 may include a single integrated circuit ("IC"), or may include a plurality of integrated circuits or other components connected, arranged or grouped together, such as microprocessors, digital signal processors ("DSPs"), application specific integrated circuits ("ASICs"), associated memory (such as RAM and ROM), and other ICs and components. As a consequence, as used herein, the term processor should be understood to equivalently mean and include a single processor, or arrangement of processors, microprocessors, controllers, or some other grouping of integrated circuits which perform the functions discussed above and also discussed in detail below with reference to FIGS. 2 and 3, with associated memory, such as microprocessor memory or additional RAM, ROM, EPROM or E²PROM. The methodology of the invention, as discussed above and as discussed below with reference to FIGS. 2 and 3, may be programmed and stored, in the processor 130 with its associated memory and other equivalent components, as a set of program instructions for subsequent execution when the processor 130 is operative (i.e., powered on and functioning).

In the preferred embodiment, the processor 130 includes a DSP 160, an analog to digital converter (A/D) 170, and a digital to analog converter (D/A) 180, with the processor 130 implemented as a DSP board within a personal computer utilizing a Signalogic PC-32 board. The personal computer may also be utilized to program and control the DSP 160. The A/D 170 is utilized to convert signals from the biological function measurements 125, such as the EKG 135 and thoracic pressure 140 signals, and from probe measurements 115, to digital form for use in the DSP 160. The DSP 160 is utilized to implement digital finite impulse response (FIR) filters and to generate a digital form of the control voltage, which is converted to analog form (for use by the piezoelectric manipulator 120) by the D/A 180.

FIG. 2 is a flow diagram illustrating a method for predictive probe stabilization relative to subject movement in accordance with the present invention. Beginning with start step 200, a probe is inserted into a prepared subject, step 205, such as inserting the probe 110 into the brain tissue of the subject 150. Subject preparation may include, for example, attachment of the various detectors and monitors (electrodes) 155 and 165, and other antecedent surgical and sterilization procedures for the selected probe measurements. Next, in step 210, a calibrated control voltage is determined from a known displacement, such as a known probe displacement, by measuring (115) probe (electrode) 110 impedance. In the preferred embodiment, this first calibration phase is performed utilizing a 1 micron (amplitude) oscillatory probe displacement at a frequency of 80–100 Hz, during which corresponding probe impedance is measured, as discussed in greater detail below. As mentioned above, this first calibration phase may also be performed by a device other than a probe 110. Next, in step 215, a second calibration phase is performed, in which control voltage parameters (e.g., filter coefficients) are determined from the calibrated control voltage (from step 210) and from the measured biological function(s) of the subject, such as from the EKG 135 and thoracic pressure 140 of the subject 150. As discussed in greater detail below, this second calibration phase is preferably implemented utilizing digital filters implemented within the DSP 160, with one filter for the EKG 135 and a second filter for the thoracic pressure 140.

Following such calibration, in step 220, the control voltage (as the input into the piezoelectric manipulator 120) is generated as a function of the measured biological function (s), utilizing the previously determined control voltage parameters. In the preferred embodiment, the total or overall control voltage is based upon a linear superposition of individual control voltages separately determined from the EKG and thoracic pressure signal inputs. The probe is then moved within the subject in response to the control voltage, step 225. This probe movement, in response to the control voltage, provides for predictive probe stabilization relative to the movement of the subject, as measured and predicted by the EKG 135 and thoracic pressure 140. With such relative stabilization of step 225, the selected, desired probe measurements are performed within the subject, step 230, and the method may end, return step 235.

As mentioned above, the DSP 160 is utilized to implement digital finite impulse response (FIR) filters, one for the signal input from the EKG 135, and one from the signal input from the thoracic pressure 140. In the preferred embodiment, the filters are implemented on a Signalogic PC-32 DSP board installed in a 150 MHz Pentium based PC, to program and control the DSP 160 utilizing host software in a MATLAB programming environment. Once the filter coefficients are computed and downloaded into the DSP 160, the assembly language code that implements the filters runs entirely independently from the host computer. The Signalogic PC-32 DSP board has four 16-bit A/ID channels (illustrated as A/ID 170) to sample and convert the relevant physiological signals, and four 16-bit DIA channels (illustrated as D/A 180), one of which is used to generate the control voltage for the piezoelectric manipulator. The input signals from the EKG 135 and thoracic pressure 140 are continuously digitized at a preferred sampling rate of 1 kHz, and stored in a circular buffers (2048 points depth) in DSP 160 memory. At every sample interval, the FIR filter for EKG and thoracic pressure (breathing) are evaluated and linearly superimposed (summed together) in the DSP 160, and sent to the D/A 180 for output. Up to four 2048-point filters running at 1 kHz may be run simultaneously on the preferred PC-32 DSP 160 implementation. In addition, filter coefficients can be updated without interrupting the filter calculations.

Three significant empirical observations are also incorporated into the preferred embodiment of the present invention. Active mechanical stabilization of a probe, such as an intracellular recording electrode, typically requires two steps: (1) measuring or inferring the motion of tissue; and (2) moving the electrode in such a way as to precisely track the motion. Most generally, this requires continuous monitoring of the tissue position in all three dimensions and a corresponding adjustment of the recording electrode in three dimensions. In accordance with the first empirical observation of the present invention, however, the fine microelectrodes that are commonly used for intracellular neuronal recording are extremely laterally compliant at the tip. More specifically, the tip moves passively with the tissue if the displacement is not along the electrode axis. As a consequence, in accordance with the present invention, active tracking of the electrode position may be limited to tracking subject movement along the direction of the electrode axis, with the compliance of the tip passively accommodating lateral movement of the subject. Under other circumstances, however, such as use of other probe types, the methodology of the present invention may be utilized in all three spatial dimensions.

The second empirical observation of the present invention concerns an observed correlation between the measured impedance of the microelectrode probe and the position of the subject tissue. More specifically, as a sharp glass microelectrode (of the type commonly used for intracellular recording) is slowly advanced through subject brain tissue, there are large fluctuations in the series electrical impedance of the electrode. The electrode impedance tends to gradually increase, presumably as the electrode tip impinges on a cellular membrane. At some point, the observed electrode impedance usually falls abruptly back to some lower value, presumably as the electrode breaks through the membrane. As a consequence, the measured electrode impedance depends on the relative position of the electrode and the brain tissue, and can therefore be used to detect brain tissue motion within the subject.

The third empirical observation of the present invention concerns an observed correlation between the measured impedance of the microelectrode probe and the cardiac and respiratory activity of the subject (as measured through EKG 135 and thoracic pressure 140). In all animals studied, the measured electrode impedance shows large fluctuations even while the electrode manipulator 120 is held stationary. These fluctuations appeared to be strongly correlated to cardiac and respiratory activity, as determined from the electrocardiogram (EKG 135) and from thoracic pressure 140, respectively. Spectral analysis of both the electrode impedance signal and the EKG 135 show spectral peaks at roughly 10–12 Hz (and higher harmonics of this frequency). Cross spectral analysis reveals that the coherence between these signals is nearly one at the spectral peaks. Analysis of the electrode impedance and the breathing signals both reveal spectral peaks at the lower respiration frequency (1–2 Hz or lower), also with a coherence of nearly one at the breathing frequency. In accordance with the present invention, the observed fluctuations in the electrode impedance are dominated by motion of the brain, which in anesthetized animals originates from two sources: cardiac and respiratory activity, and that the electrode impedance is a sensitive detector of such relative brain motion. These observations are utilized in the preferred embodiment of the invention, as illustrated with respect to FIG. 3.

Underlying the implementation of the preferred method illustrated in FIG. 3 is the determination of the control voltage, $V_{CONTROL}(t)$, which at a current time step is given by the FIR equation:

$$V_{CONTROL}(t)=\Sigma_i a_i V_{BIO}(t_i), \; t_i=t-i*\Delta t, \; i=0\ldots N \quad \text{(Equation (1))}$$

where "N" is the number of FIR coefficients, the summation is over all "i", $a_i$ are the N coefficients of the FIR filter, $V_{BIO}(t_i)$ are the N-most recent values of the measured biological function (such as EKG voltage or thoracic pressure), and $\Delta t$ is the sampling interval. If an optimal control voltage $V_{OPT}(t)$ were known over some long time interval, then the filter coefficients could be determined as those that minimize the squared error (E) between the optimal control voltage and the (actual) control voltage:

$$E_{min}=\min[a_i]\Sigma|V_{OPT}(t)-V_{CONTROL}(t)|^2 \quad \text{(Equation (2))}$$

In accordance with the present invention, because the optimal time-dependent control voltage that stabilizes the electrode is not known a priori, the optimal control voltage $V_{OPT}(t)$ may be inferred from and set equal to a calibrated control voltage $V_{CAL}(t)$. This calibrated control voltage $V_{CAL}(t)$ is inferred from the electrode impedance signal Z(t) using the relationship $V_{CAL}(t)=G*Z(t)$, where G is the slope of the relationship between piezo manipulator 120 control voltage and electrode impedance. Since G is a function of electrode position, this may be a nonlinear relationship. In accordance with the present invention, however, the best overall results were obtained by using the average value of G ($\overline{G}$), where $\overline{G}$ is determined by dithering the piezo manipulator 120 control voltage at a high frequency (80 Hz) and measuring the fluctuations in the electrode impedance.

The vector of coefficients [a] that produce the least squared error described above (Equation (2)), in the preferred embodiment, is derived in the frequency domain from the transfer function $$A(\omega)=S_{XY}(\omega)/S_{XX}(\omega), \quad \text{(Equation (3))}$$

where $S_{XY}(\omega)$ is the cross spectral density between the calibrated control voltage signal $V_{CAL}(\omega)$ ($V_{CAL}(t)$ converted into frequency domain) (as inferred above) and $V_{BIO}(\omega)$ ($V_{BIO}(t)$ also converted into frequency domain), and $S_{XX}(\omega)$ is the spectral density of $V_{BIO}(\omega)$. The spectral densities are estimated using multitaper spectral techniques.

In addition, because the measured biological functions (such as the EKG) may be highly periodic, this transfer function may only be defined at the fundamental frequency and the harmonics of the fundamental frequency. As a consequence, the transfer function is multiplied by a linear phase shift to make the phase reasonably flat, intermediate (non-harmonic) values of the real and imaginary parts of the transfer function are determined by cubic-spline interpolation, followed by multiplying the interpolated function by a the linear phase shift of the same magnitude but opposite sign. Because the breathing signal is usually less periodic, the harmonic components are often slightly overlapped, and as a result, the transfer function for the breathing signal can be used directly without such additional interpolation. The time domain coefficients $a_i(t)$ (impulse response) are found as the inverse Fourier transform of the transfer function $A(\omega)$, and the FIR coefficients for each signal (EKG and thoracic pressure) are then downloaded into the DSP board. The resulting individual control voltages, for each EKG and thoracic pressure input, are then linearly superimposed to generate an overall control voltage input into the piezoelectric manipulator 120. This methodology is summarized in FIG. 3.

FIG. 3 is a flow diagram illustrating, in greater detail, a preferred method for predictive probe stabilization relative to subject movement in accordance with the present invention. Beginning with start step 300, a probe is inserted into a prepared subject, step 305, as discussed above. Next, the probe (or other device) is moved through a known displacement, preferably the 1 micron oscillation at 80–100 Hz, and the probe impedance Z(t) is measured (to determine "$\overline{G}$", an average value of "G"), followed by determine a calibrated control voltage $V_{CAL}(t)$ as $V_{CAL}(t)=Z(t)$, steps 310 and 315. Fourier transforms are then determined for $V_{CAL}(t)$ and $V_{BIO}(t)$, the voltage representations of the measured biological functions, such as cardiac and respiratory functions, to form $V_{CAL}(\omega)$ and $V_{BIO}(\omega)$, step 320. The cross spectral density $S_{XY}(\omega)$ of $V_{CAL}(\omega)$ and $V_{BIO}(\omega)$, and the spectral density $S_{XX}(\omega)$ of $V_{BIO}(\omega)$ are determined, steps 325 and 330.

Filter coefficients in the frequency domain are determined as $A(\omega)=S_{XY}(\omega)/S_{XX}(\omega)$, step 335, followed by performing an inverse Fourier transform to determine filter coefficients as, step 340. In the preferred embodiment, steps 310 through 340 are repeated (iterated) several times, utilizing previously obtained values of $a_i$, with values for $a_i$ updated with each subsequent iteration. The control voltage is generated as a linear superposition of all individual control voltages, preferably one for cardiac function and one for respiratory function, where each individual control voltage is determined as $V_{CONTROL}(t)=\Sigma_i a_i V_{BIO}(t)$, and converted to analog form, step 345. The probe is then moved within the subject in response to the control voltage, step 350, desired probe measurements are made, step 355, and the method may end, return step 360.

Numerous advantages of the present invention may be apparent from the above discussion. The method and system of the present invention provide for probe stabilization, relative to subject movements for accurate measurement within a live subject. The probe stabilization of the present invention is predictive or active, anticipating subject movement which may otherwise interfere with accurate measurements. In addition, the method and system of the present invention do not alter or interfere with the physiological states of the subject, and otherwise minimizes contact with the subject tissue, to avoid interfering with the processes under study, to avoid tissue damage, and also to avoid other potential sources of error.

From the foregoing, it will be observed that numerous variations and modifications may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

It is claimed:

1. A method for predictive probe stabilization, the probe stabilization relative to movement of a subject, the method comprising:
   (a) inserting a probe into the subject, the probe moveable in response to a control voltage;
   (b) determining a calibrated control, voltage from a known displacement;
   (c) determining a plurality of control voltage parameters from the calibrated control voltage and from a measured biological function of the subject;
   (d) generating the control voltage from the measured biological function and from the plurality of control voltage parameters; and
   (e) moving the probe within the subject in response to the control voltage.

2. The method of claim 1, further comprising:
   (f) performing probe measurements within the subject.

3. The method of claim 1, wherein the measured biological function is an electrocardiogram as a measurement of cardiac function of the subject.

4. The method of claim 1, wherein the measured biological function is thoracic pressure as a measurement of respiratory function of the subject.

5. The method of claim 1, wherein step (d) further comprises:
   generating the control voltage as a linear superposition of a first intermediate control voltage determined from a first plurality of control voltage parameters and an electrocardiogram as a first measured biological function, and a second intermediate control voltage determined from a second plurality of control voltage parameters and thoracic pressure as a second measured biological function.

6. The method of claim 1, wherein step (b) further comprises:
   measuring an impedance of the probe during a known oscillatory movement having a known amplitude and frequency.

7. The method of claim 1, wherein step (c) further comprises:
   determining the plurality of control voltage parameters as a plurality of finite impulse response (FIR) filter coefficients $a_i$;
   determining the plurality of FIR filter coefficients $a_i$ as inverse Fourier transforms of a corresponding plurality of coefficients $A(\omega)$, wherein the plurality of coefficients $A(\omega)$ are determined in a frequency domain from a transfer function:

$$A(\omega) = S_{XY}(\omega)/S_{XX}(\omega);$$

in which $S_{XY}(\omega)$ is a cross spectral density between the calibrated control voltage converted into frequency domain as $V_{CAL}(\omega)$ and the measured biological function converted into frequency domain as $V_{BIO}(\omega)$, and $S_{XX}(\omega)$ is a spectral density of $V_{BIO}(\omega)$.

8. The method of claim 7, wherein step (d) further comprises determining the control voltage $V_{CONTROL}(t)$ as:

$$V_{CONTROL}(t) = \Sigma_i a_i V_{BIO}(t_i), \; t_i = t - i^* \Delta t, \; i=0 \ldots N;$$

in which "N" is a number of the finite impulse response (FIR) filter coefficients $a_i$, "t" is a time value, summation "$\Sigma$" is over all "i", "$a_i$" are N FIR filter coefficients, "$V_{BIO}(t_i)$" is a plurality of N-most recent values of the measured biological function, and "$\Delta t$" is a sampling interval.

9. The method of claim 7 wherein the plurality of FIR filter coefficients $a_i$ at non-harmonic frequencies of the measured biological function are determined by cubic-spline interpolation.

10. The method of claim 1, wherein probe movement in response to the control voltage is in a direction of the probe axis.

11. The method of claim 1, wherein probe movement in a direction lateral to the probe axis is passive.

12. The method of claim 1, wherein the probe is a microelectrode.

13. The method of claim 1, wherein the probe is a microscopic instrument.

14. The method of claim 1, wherein the probe is a surgical instrument.

15. The method of claim 1, wherein the probe is a fiber-optic scope.

16. The method of claim 1, wherein the probe is a microscope.

17. A system for predictive probe stabilization, the probe stabilization relative to movement of a subject, the system comprising:
   a manipulator, the manipulator couplable to a probe, the manipulator operable to move the probe in response to a control voltage; and
   a processor, the processor having an output coupled to the manipulator, the processor having a plurality of inputs to receive a measured biological function of the subject and to receive a calibration measurement, wherein the processor includes instructions to determine a calibrated control voltage from a known displacement, to determine a plurality of control voltage parameters from the calibrated control voltage and from a measured biological function of the subject, and to generate the control voltage at the output from the measured biological function and from the plurality of control voltage parameters.

18. The system of claim 17, wherein the processor further comprises:
   a multi-channel analog-to-digital converter forming the plurality of inputs;
   a digital signal processor; and
   a digital-to-analog converter forming the output.

19. The system of claim 17, further comprising:
   an electrocardiograph coupled to the subject and coupled to a first input of the plurality of inputs of the processor to generate the measured biological function as an electrocardiogram, as a measurement of cardiac function of the subject.

20. The system of claim 17, further comprising:
a pressure detector coupled to the subject and coupled to a second input of the plurality of inputs of the processor to generate the measured biological function as thoracic pressure, as a measurement of respiratory function of the subject.

21. The system of claim 17, wherein the processor includes further instructions to generate the control voltage as a linear superposition of a first intermediate control voltage determined from a first plurality of control voltage parameters and an electrocardiogram as a first measured biological function, and a second intermediate control voltage determined from a second plurality of control voltage parameters and thoracic pressure as a second measured biological function.

22. The system claim 17, wherein the calibration measurement includes an impedance measurement of the probe during a known oscillatory movement having a known amplitude and frequency.

23. The system of claim 17, wherein the processor includes further instructions to determine the plurality of control voltage parameters as a plurality of finite impulse response (FIR) filter coefficients $a_i$; and to determining the plurality of FIR filter coefficients $a_i$ as inverse Fourier transforms of a corresponding plurality of coefficients $A(\omega)$, wherein the plurality of coefficients $A(\omega)$ are determined in a frequency domain from a transfer function:

$$A(\omega)=S_{XY}(\omega)/S_{XX}(\omega);$$

in which $S_{XY}(\omega)$ is a cross spectral density between the calibrated control voltage converted into frequency domain as $V_{CAL}(\omega)$ and the measured biological function converted into frequency domain as $V_{BIO}(\omega)$, and $S_{XX}(\omega)$ is a spectral density of $V_{BIO}(\omega)$.

24. The system of claim 23, wherein the processor includes further instructions to determine the control voltage $V_{CONTROL}(t)$ as:

$$V_{CONTROL}(t)=\Sigma_i a_i V_{BIO}(t_i), t_i=t-i^*\Delta t, i=0\ldots N;$$

in which "N" is a number of the finite impulse response (FIR) filter coefficients $a_i$, "t" is a time value, summation "$\Sigma$" is over all "i", "$a_i$" are N FIR filter coefficients, "$V_{BIO}(t_i)$" is a plurality of N-most recent values of the measured biological function, and "$\Delta t$" is a sampling interval.

25. The system of claim 23 wherein the processor includes further instructions to determine by cubic-spline interpolation the plurality of FIR filter coefficients a; at non-harmonic frequencies of the measured biological function.

26. The system of claim 17, wherein movement of the manipulator in response to the control voltage is in a direction of the probe axis.

27. The system of claim 17, wherein probe movement in a direction lateral to the probe axis is passive.

28. The system of claim 17, wherein the probe is a microelectrode.

29. The system of claim 17, wherein the probe is a microscopic instrument.

30. The system of claim 17, wherein the probe is a surgical instrument.

31. The system of claim 17, wherein the probe is a fiber-optic scope.

32. The system of claim 17, wherein the probe is a microscope.

33. A system for predictive probe stabilization, the probe stabilization relative to movement of a subject, the system comprising:
a manipulator, the manipulator removably attachable to a probe, the manipulator operable to move the probe in response to a control voltage;
an electrocardiograph coupled to the subject to measure cardiac function as a first measured biological function;
a pressure detector coupled to the subject to measure respiratory function as a second measured biological function; and
a processor, the processor having as a digital-to-analog converter as an output coupled to the manipulator, the processor having a multi-channel analog-to-digital converter coupled to the electrocardiograph to receive the first measured biological function, coupled to the pressure detector to receive the second measured biological function, and further coupled to the probe to receive a probe measurement of a known probe displacement, wherein the processor includes instructions to determine a calibrated control voltage from the probe measurement, and to determine a first plurality of filter coefficients from the calibrated control voltage and from the first measured biological function, and to generate a first intermediate control voltage from the first measured biological function and from the first plurality of filter coefficients, wherein the processor includes further instructions to determine a second plurality of filter coefficients from He calibrated control voltage and from the second measured biological function, and to generate a second intermediate control voltage from the second measured biological function and from the second plurality of filter coefficients; and wherein the processor includes further instructions to generate the control voltage as a linear superposition of the first intermediate control voltage and the second intermediate control voltage.

34. The system claim 33, wherein the probe measurement includes an impedance measurement of the probe during a known oscillatory movement having a known amplitude and frequency.

35. The system of claim 33, wherein the processor includes further instructions to determine the first and second pluralities of filter coefficients as inverse Fourier transforms of corresponding first and second pluralities of coefficients $A(\omega)$, wherein the first and second pluralities of coefficients $A(\omega)$ are determined in a frequency domain from a transfer function:

$$A(\omega)=S_{XY}(\omega)/S_{XX}(\omega);$$

in which $S_{XY}(\omega)$ is a cross spectral density between the calibrated control voltage converted into frequency domain as $V_{CAL}(\omega)$ and, respectively, a first measured biological function converted into frequency domain as $V_{BIO}(\omega)$ or a second measured biological function converted into frequency domain as $V_{BIO}(\omega)$, and $S_{XX}(\omega)$ is a spectral density of the respective $V_{BIO}(\omega)$; and wherein the processor includes further instructions to determine by cubic-spline interpolation the respective first and second pluralities of filter coefficients at respective non-harmonic frequencies of the first and second measured biological functions.

36. The system of claim 35, wherein the processor includes further instructions to determine, respectively, the first and second intermediate control voltages $V_{CONTROL}(t)$ as:

$$V_{CONTROL}(t)=\Sigma_i a_i V_{BIO}(t_i), t_i=t-i^*\Delta t, i=0\ldots N;$$

in which "N" is a number of the filter coefficients $a_i$, "t" is a time value, summation "$\Sigma$" is over all "i", "$a_i$" are N filter coefficients, "$V_{BIO}(t_i)$" is a plurality of N-most recent values of the respective first or second measured biological functions, and "$\Delta t$" is a sampling interval.

* * * * *